US00PP13987P39

(12) United States Plant Patent
Kanno

(10) Patent No.: US PP13,987 P3
(45) Date of Patent: Jul. 15, 2003

(54) OSTEOSPERMUM PLANT NAMED 'KAKEGAWA AU8'

(75) Inventor: Masao Kanno, Chigasaki (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/971,676

(22) Filed: Oct. 9, 2001

(65) Prior Publication Data

US 2003/0070199 P1 Apr. 10, 2003

(51) Int. Cl.[7] ..... A01H 5/00

(52) U.S. Cl. ..... Plt./360

(58) Field of Search ..... Plt./360

*Primary Examiner*—Bruce R. Campell
*Assistant Examiner*—Annette H. Para
(74) *Attorney, Agent, or Firm*—Jondle & Associates PC

(57) ABSTRACT

An Osteospermum plant particularly distinguished by its violet flower color and tendency to hold flowers open later in the evening.

1 Drawing Sheet

Genus and species: *Osteospermum fruiticosum.*
Variety denomination: 'Kakegawa AU8'.

BACKGROUND OF THE NEW PLANT

The present invention originated in 1994 from an $F_1$ selection of *Osteospermum fruiticosum.* The female parent was known as breeding line No. 375 and possessed large, white flowers. The male parent was known as line No. 471 and possessed large flowers that would stay open later into the evening than most Osteospermums. Line No. 375 originated from a hybridization made in 1991 between an $F_5$ selection from a cross between a pink flowered line and a white with blue eye line, and a dwarf habit breeding line with flowers that stayed open late. Line No. 471 originated from a hybridization made in 1993 between a dwarf, rose flowered line with flowers that stayed open late and a dwarf, pink flowered line. The origin of these lines dates back to crosses made by the inventor in 1984. The original selection made in 1995 was vegetatively propagated again in 1996 and stability was confirmed in 1997. The line was established as 'Kakegawa AU8', and determined to have its characteristics firmly fixed.

DESCRIPTION OF PHOTOGRAPH

This new Osteospermum plant is illustrated by the accompanying photograph which shows blooms, and foliage of the plant in full color, the colors shown being as true as can be reasonably obtained by conventional photographic procedures.

DESCRIPTION OF THE NEW CULTIVAR

Figure 1:
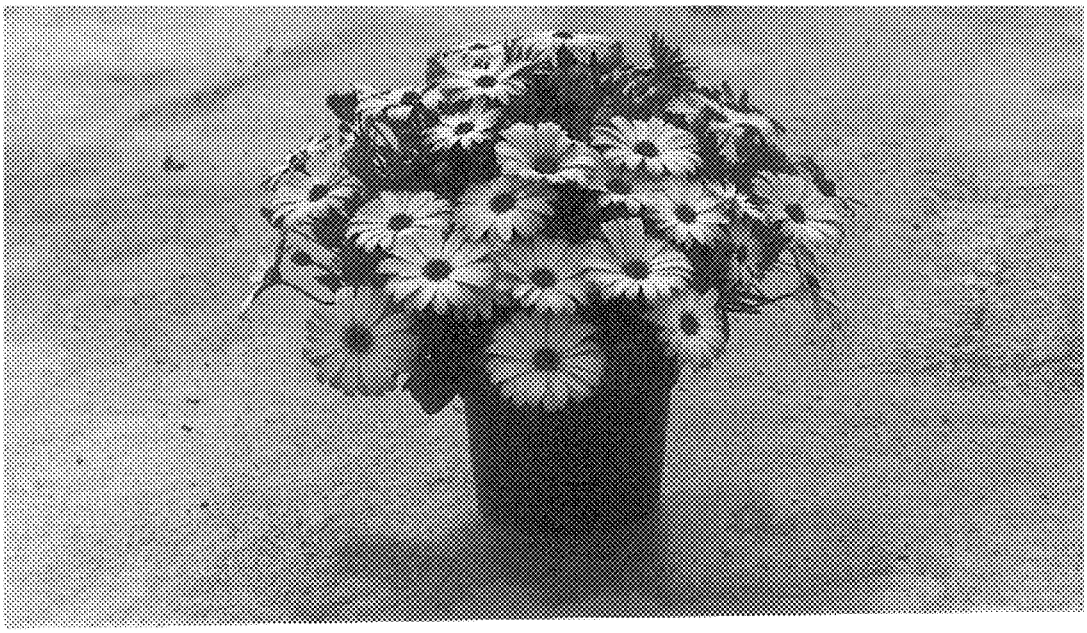
FIG. 1 shows a view of three plants propagated in a 20 cm diameter pot.
Figure 2:
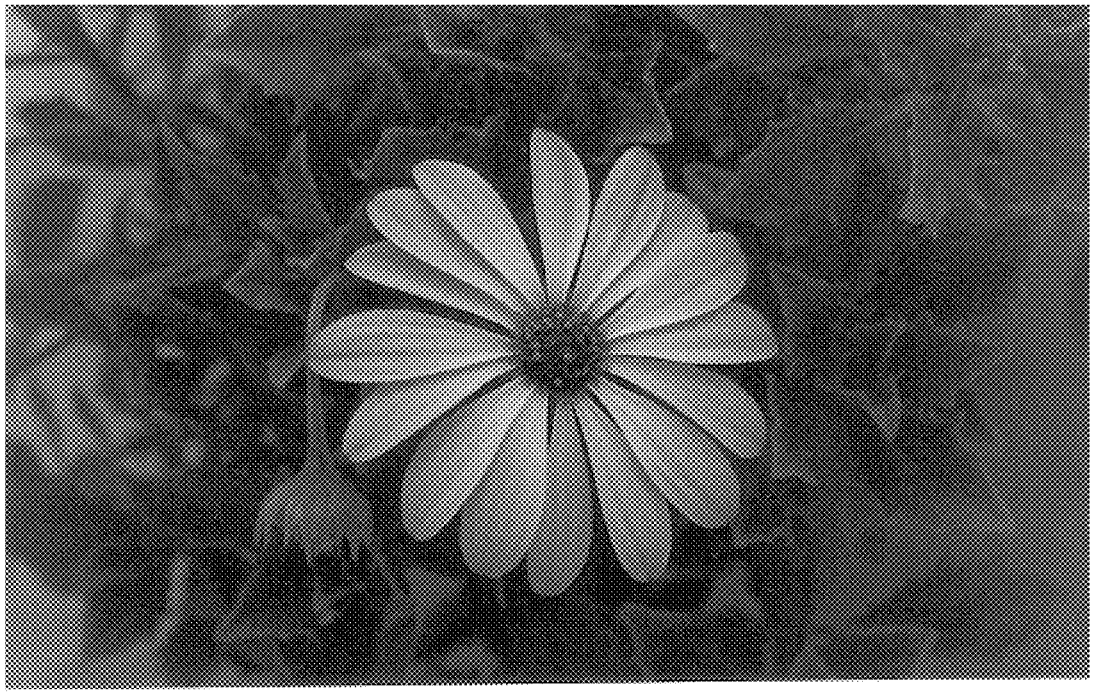
FIG. 2 shows a close-up view of a single inflorescence.

The following detailed descriptions set forth the distinctive characteristics of 'Kakegawa AU8'. The data which defines these characteristics were collected from asexual reproductions carried out in Salinas, Calif. Three plants from fully rooted 20 cm diameter pots and grown in the same conditions. Data was collected on plants 28 weeks from transplanting rooted cuttings into 16 cm diameter pots and growing as described below. Color references are to The R.H.S. Colour Chart of The Royal Horticultural Society of London (R.H.S.).

DESCRIPTION OF THE NEW PLANT

Classification:
- *Family.*—Compositae.
- *Botanical.*—*Osteospermum fruticosum.*
- *Commercial.*—Cape daisy.

Parentage:
- *Female parent.*—Breeding line No. 375 (unpatented).
- *Male parent.*—Breeding line No. 471 (unpatented).

Growth:
- *Time to produce a rooted cutting.*—Cuttings will colonize a 2.5 cm diameter by 2.5 cm tall greenhouse tray cell with peat-based plant media in approximately five weeks. Cuttings are dipped in a normal dilution (1:9) of Dip 'N Grow™ root inducing solution in water. The trays are misted hourly during rooting.
- *Environmental conditions for plant growth.*—Rooted cuttings are transplanted to pots with a 16 cm diameter, one plant per pot. Peat moss-based growing media is used. The pots are watered using a 150–200 ppm fertilizer solution containing 18% nitrogen, 8% phosphorus and 18% potassium. The soil is allowed to dry between waterings. During the first few weeks after transplanting the plants should have evening temperatures around 15–18° C. for good root growth. When plants reach 7.5–10 cm in height they are pinched back to 5–6 leaves to promote branching. The plants are grown through the winter in cool greenhouses (10–15° C.) with no shading to keep their habit compact. In spring, after the plants have received at least four weeks of cool conditions to vernalize, warmer temperatures can be used to promote blooming. Spring and summer daytime high temperatures in Salinas, Calif., where the data was collected, range from 16–25° C.
- *Time to bloom from propagation.*—18–20 weeks when rooted vegetative cuttings are transferred to a 16 cm diameter pot in late Fall and given several weeks of below 50° F. temperature prior to increasingly warmer spring weather.
- *Habit.*—Vigorous, well branched.
- *Life cycle.*—Perennial.

Plant:
*Form.*—Upright.
*Plant size.*—Height is 35–40 cm; width is 35–40 cm.
Stems:
*Internode length.*—0.8–1.0 cm.
*Color.*—Yellow-green (RHS N144A).
*Description.*—Strong, erect, herbaceous.
*Stem diameter.*—3.0–4.0 mm.
*Stem length.*—With pinching stems back to 5 or 6 leaves to promote branching, stems will terminate with petioles at about 10–14 cm.
*Pubescence.*—Short, transparent.
*Peduncle length.*—9–12 cm.
*Peduncle diameter.*—2.5–3.0 cm.
*Peduncle color.*—Yellow-green RHS N144A.
Leaves:
*Arrangement.*—Alternate.
*Shape.*—Spatulate.
*Length.*—Up to 6.5 cm.
*Width.*—Up to 3.5 cm.
*Apex.*—Mucronate.
*Base.*—Oblique, sessile.
*Margin.*—Dentate.
*Venation.*—Pinnate.
*Color.*—Upper is green (RHS 137A); Lower is green (RHS 137C).
*Venation.*—Upper surface is green RHS 137A; lower surface is green RHS 137C.
Inflorescence:
*Type.*—Capitulum (head); disc florets are staminate and ray florets are carpellate.
*Diameter.*—7.0–8.0 cm.
*Depth.*—2.5–3.5 cm when fully open.
*Disc diameter.*—2.0 cm.
*Lastingness of the individual inflorescence.*—7–10 days.
*Habit.*—Determinate.
*Fragrance.*—None.
*Fruit and seed.*—None.
Phyllaries:
*Description.*—13–16 phyllaries, arranged symmetrically.
*Shape.*—Linear.
*Apex.*—Acute.
*Size.*—Length is 1.2–1.4 cm; Width is 2.0–3.0 mm.
*Margin.*—Entire.
*Color.*—Upper is green (RHS 137D) and lower is green (RHS 138C).
Ray florets:
*Corolla.*—One ray per floret on outer whorl of flowers. Only the outer row of florets are the ray florets.
*Ray florets.*—14–18.
*Ray floret size.*—Length of ray florets is 3.8–4.0 cm; width is 1.0 cm.
*Ray floret shape.*—Spatulate.
*Ray floret apex.*—Obtuse with indentation at tip.
*Ray floret margin.*—Entire.
*Ray floret color.*—Ventral surface of ray florets is red-purple (RHS 70B) with white shading; dorsal surface of floret is purple (RHS 79C) with purple-violet (RHS N82C) veins.
*Ovary.*—Inferior.
*Style form.*—One style with two stigma branches.
*Style color.*—Purple (RHS 75B).
*Stigma color.*—Purple (RHS N79A).
*Pistil.*—One per ray floret.
*Pistil length.*—5 mm.

Inflorescence bud:
*Bud shape.*—Tubular.
*Bud size.*—Length is 5 mm and width is 1 mm.
*Color of bud tip.*—Violet-blue (RHS N93A).
Disc florets:
*Number per head.*—30–35.
*Disc florets shape.*—Tubular.
*Disc florets length.*—5 mm at bud stage; 7 mm at mature floret.
*Disc florets width.*—1 mm.
*Disc florets apex.*—Rounded.
*Disc florets color.*—Without dissecting the florets from the inflorescence head, they are violet-blue RHS N93A at bud stage; purple RHS N77A when anthers emerge and yellow-orange RHS 17A when anthers shed pollen.
*Anther color.*—Purple (RHS N77A).
*Filament color.*—Yellow (RHS 4D).
*Pollen color.*—Yellow-orange (RHS 17A).

Disease and Insect Resistance

No susceptibility to diseases or insects noted to date.

Comparison with Known Cultivars

'Kakegawa AU8' is most similar to the variety 'Kakegawa AU2', the subject of U.S. Plant patent application Ser. No. 09/657,540 which is marketed under the name 'Sea Mist Pink and White'. The two plants differ as shown in Table 1 below.

TABLE 1

| Characteristic | 'Kakegawa AU8' | 'Kakegawa AU2' |
|---|---|---|
| Leaf margin | Highly serrated | Slightly serrated |
| Flower diameter | 7.0–8.0 cm | 5.5–6.0 cm |
| Ray floret length | 3.8–4.0 cm | 2.5–3.0 cm |
| Ray floret color | Ventral surface is red-purple (RHS 70B) with white shading; dorsal surface of ray floret purple (RHS 79C) | Ventral surface is red-purple (RHS 70B) with the lower portion of the ray floret white (RHS 155C); dorsal surface is red-purple (RHS 71A) |
| Veins | On dorsal petal surface are purple-violet (RHS N82C) | On dorsal petal surface are violet (RHS 83B) |

In Table 2 below, some of the differences of 'Kakegawa AU8' as compared to parental cultivars 375 and 471 are shown:

TABLE 2

| Characteristic | 375 | 471 | AU8 |
|---|---|---|---|
| Plant habit | Semi-dwarf upright | Semi-dwarf upright | Large upright |
| Plant height | 20–25 cm | 25–30 cm | 35–40 cm |
| Ray floret color upper | White w/pink stripes | Rose | Red-purple |
| Ray floret color lower | White | White | Purple |
| Bloom under low light | Semi-closed | Semi-closed | Open |
| Leaf Color | Lt. Green | Dk. Green | Dk. Green |

I claim:

1. A new and distinct Osteospermum plant as shown and described herein.

* * * * *